(12) United States Patent
Demassa

(10) Patent No.: US 10,421,851 B2
(45) Date of Patent: Sep. 24, 2019

(54) LOW EMISSIONS SCORCH INHIBITOR FOR POLYURETHANE FOAM

(71) Applicant: VANDERBILT CHEMICALS, LLC, Norwalk, CT (US)

(72) Inventor: John M. Demassa, Trumbull, CT (US)

(73) Assignee: VANDERBILT CHEMICALS, LLC

( * ) Notice: Subject to any disclaimer, the term of this patent is extended or adjusted under 35 U.S.C. 154(b) by 91 days.

(21) Appl. No.: 15/720,625

(22) Filed: Sep. 29, 2017

(65) Prior Publication Data

US 2018/0094120 A1 Apr. 5, 2018

Related U.S. Application Data

(60) Provisional application No. 62/402,279, filed on Sep. 30, 2016.

(51) Int. Cl.

| | | |
|---|---|---|
| C08K 5/3437 | (2006.01) | |
| C08G 18/76 | (2006.01) | |
| C08G 18/48 | (2006.01) | |
| C08G 18/16 | (2006.01) | |
| C08K 5/00 | (2006.01) | |
| C07D 215/12 | (2006.01) | |
| C08L 75/04 | (2006.01) | |
| C08G 101/00 | (2006.01) | |

(52) U.S. Cl.
CPC .......... *C08K 5/3437* (2013.01); *C07D 215/12* (2013.01); *C08G 18/165* (2013.01); *C08G 18/4816* (2013.01); *C08G 18/4829* (2013.01); *C08G 18/7621* (2013.01); *C08K 5/0066* (2013.01); *C08L 75/04* (2013.01); *C08G 2101/0016* (2013.01); *C08G 2101/0083* (2013.01); *C08L 2201/02* (2013.01)

(58) Field of Classification Search
CPC ... C08K 5/3437; C08L 75/04; C08L 2201/02; C07D 215/12; C08G 2101/0016
See application file for complete search history.

(56) References Cited

U.S. PATENT DOCUMENTS

| | | | |
|---|---|---|---|
| 6,224,791 B1 * | 5/2001 | Stevenson | C08K 5/1535 252/589 |
| 6,235,686 B1 | 5/2001 | Karol et al. | |
| 6,569,927 B1 * | 5/2003 | Gelbin | C08K 5/005 524/107 |
| 6,599,927 B2 | 7/2003 | Lindberg et al. | |
| 2002/0032247 A1 | 3/2002 | Ragsdale et al. | |
| 2011/0230579 A1 | 9/2011 | Demassa | |
| 2014/0039077 A1 | 2/2014 | Magness | |
| 2015/0307676 A1 | 10/2015 | Demassa | |

OTHER PUBLICATIONS

Ciba Irganox 1076 MSDS (Year: 2004).*
Tokyo chemical industry co ltd. CAS RN: 164391-52-0 MSDS (Year: 2019).*
International Search Report dated Nov. 17, 2017, dated Dec. 14, 2017.

* cited by examiner

*Primary Examiner* — Peter F Godenschwager
*Assistant Examiner* — Andrew J. Oyer
(74) *Attorney, Agent, or Firm* — Norris McLaughlin, P.A.

(57) ABSTRACT

Disclosed is a scorch inhibitor composition comprising (A) one or more 2,2,4-trimethyl-1,2-dihydroquinoline compound, (B) one or more lactone, (C) one or more phenolic compound, (D) optionally one or more tocopherol, and (E) optionally one or more phosphite compound.

16 Claims, No Drawings

LOW EMISSIONS SCORCH INHIBITOR FOR POLYURETHANE FOAM

This U.S. Non-provisional application claims benefit of U.S. Provisional Application No. 62/402,279, filed Sep. 30, 2016, the disclosure of which patent application is incorporated herein by reference.

DETAILED DESCRIPTION OF INVENTION

This invention is useful as a scorch inhibitor for polyurethane (PUR) foam having the additional attribute of low volatile chemical emissions. Specifically, the invention is a three to five component blend that provides scorch protection for slabstock polyurethane foam during production and offers reduced volatile organic compounds as measured by VOC/fog emissions test known as VDA-278. VDA-278 is a Thermodesorption technique used to determine volatile components.

Typically, polyurethanes are a class of condensation polymer composed of two principle compounds including toluene diisocyanate (TDI-usually a mixture of 2,4- and 2,6-isomers) and a polyol or diol of varying molecular weights (Paul. C. et al., Fundamentals of Polymer Science, Technomic Publishing Co., Inc. Technomic Publishing Co., Lancaster, Pa. 1994, 433 pp., ISBN 1-56676-152-2, p. 36). Water can be added to the reaction mixture that results in in situ generation of $CO_2$ from hydrolysis of the TDI component which converts the polymer mass into a foam. During the manufacture of polyurethane slabstock foam, a vigorous exothermic reaction is observed (M. P. Luda et. al, Discoloration in fire retardant flexible polyurethane foams. Part I. Characterization, Polymer Degradation and Stabilization, 83 (2004), p.215). It is generally understood to be the result of the exotherm resulting from the gel reaction or polycondensation reaction between polyol and diisocyanate components and the "blow reaction," which is $CO_2$ production (Brian Kaushiva, Structure-Property Relationships Of Flexible Polyurethane Foams, Ph.D. Thesis, Virginia Polytechnic Institute and State University, 1999, p. 5). The reported heat of reaction is approximately 24 kcal/mol of urethane and 47kcal/mol of urea. Visually, a darkened yellow to brown discoloration known as scorch in the core of the production foam block develops, resulting from undissipated heat. Investigators have shown that complex free radical reactions drive the scorching process. (Y. Su, Wang Wan Jiang, Thermal Stability of Poly(oxypropylene-ether) Polyol, Thermochimica Acta, 123 (1988) 221-231). Discoloration in the scorched area of water-blown PUR foam has also been attributed to oxidation of non-polymeric additive components. (M. P.Luda et al.). Components such as aromatic amines, phenolic compounds and flame retardants are altered during foam processing, leading to highly colored conjugated species. For example, a typical phenolic compound such as butylated hydroxytoluene (BHT) is converted to a quinone dimer, which is highly discoloring even at concentration levels of 150 ppm (Jan C. J. Bart, Polymer additive analytics: industrial practice and case studies, p.51).

The invention is a scorch inhibitor blend (or antioxidant) used to reduce the phenomenon known as scorch appearing as dark charring found in the polyurethane foam block interior after production. The present invention apparently suppresses free radical auto-oxidation reactions thereby reducing darkening. The components in the blend include (A)-(C) and optionally may include other components (D)-(E):

(A) 2,2,4-trimethyl-1,2-dihydroquinoline compounds
(B) lactones
(C) Phenolic compounds
Other optional compounds:
(D) Tocopherols
(E) compounds such as phosphites and phosphonites.

Relevant disclosures can be found in U.S. Pat. Nos. 5,516,920, 5,367,008, 5,369,159 and 5,428,162 issued to Peter Nesvadba et al. Further, 3-arylbenzofuranones polymeric compounds are taught in U.S. Pat. No. 7,390,912 issued to Xia et al. (hereinafter "Xia") As compared to technology using lactones taught by Xia, the present invention improves upon scorch performance showing a synergistic effect. Unexpectedly, it has been discovered that each component of the blend shows poor scorch inhibition during polyurethane foam preparation, while the composite blend at equal loading in the foam composition is superior to individual components thereby showing synergism.

It has been discovered that by combining (A) a polymerized trimethyl quinoline compound, (B) a lactone and (C) a phenolic compound, the resulting blend in PUR foam testing shows lower emission profiles as detected upon VDA-278 testing. These blends may optionally include compounds (D) and/or (E) within the scope of the proposed composition.

The types of compounds within the groups mentioned are more specifically defined as follows:

Component A—2,2,4-trimethyl-1,2-dihydroquinoline Compounds

This component shall consist of polymers and or mixtures of polymers and oligomers of this class, including an aromatized 1,2-dihydro-2,2,4-trimethylquinoline polymer with predominantly 2 to 6 monomer units (and its derivatives as taught in U.S. Pat. No. 2,908,646); and a non-aromatized 1,2-dihydro-2,2,4-trimethylquinoline composed of dimer and trimer units (as taught in U.S. Pat. No. 6,235,686).

In an embodiment of the present invention, examples of Component A include quinolines such as 6-dodecyl-2,2,4-2,2,4-trimethyl-1,2-dihydroquinoline(6-lauryl-2,2,4-trimethyl-1H-quinoline) (CAS: 89-28-1), 6-ethoxy-2,2,4-trimethyl-1-2-dihydroquinoline (CAS: 91-53-2), polymerized 1,2-dihydro-2,2,4-trimethylquinoline (CAS: 26780-96-1) and the like.

Component B—Lactones

It is preferred that the lactones be a liquid or that where there is a mixture of lactones used the mixture itself is a liquid (thus a combination of solid and liquid lactones resulting in a liquid mixture is desirable).

The lactones may be 3-alkyl- benzofurane-2-ones or 3-aryl-benzofurane-2-ones that may have low molecular weights as taught in U.S. Pat. Nos. 5,367,008, 5,369,159 and 5,428,162 (Nesvadba). In addition, they may be polymeric compounds of said 3-alkyl- benzofurane-2-ones and said 3-aryl-benzofurane-2-ones as taught for example in Xia. An example of a 3-aryl-benzofurane-2-one is 5,7-di-tert-butyl-3-(3,4-dimethylphenyl)3H-benzofuran-2-one. Examples of a 3-alkyl-benzofurane-2-one include 2(3H)-benzofuranone, 5,7-bis-(1,1-dimethylethyl)-3-hydroxy-, reaction products with (o)-xylene. In an embodiment the polymeric or oligomeric 3-aryl-benzofurane-2-one possesses on its aryl ring polymers or oligomers of ethylene oxide/propylene oxide or a combinations thereof.

Other aromatic ring substitution derivatives of these classes are also included as exemplified by 5,7-bis-(1,1-dimethylethyl)-3- hydroxy-, reaction products with (o)-xylene and other 3-(alkoxyphenyl) benzofuran-2-ones and 3-(acyloxyphenyl) benzofuran-2-one derivatives. Also included within the group are less substituted benzofuranones such as 2(3H)-benzofuranone for which mixtures of these are also contemplated. Non-aromatic lactones such as gamma-butyrolactone, delta-gluconolactone, and gamma-undecalactone, and mixtures thereof are also contemplated as within the scope of the present invention.

In an embodiment of the present invention, component B is a polymeric, and/or mixtures with lower molecular weight lactones such as 5,7-di-tert-butyl-3-(3,4-dimethylphenyl) 3H-benzofuran-2-one. Further specific examples of Component B include xylyl dibutylbenzofuranone 2(3H)-benzofuranone, 5,7-bis(1,1-dimethylethyl)-3-hydroxy-, reaction products with o-xylene (CAS: 181314-48-7) and/or a mixture of 90% of 5,7-di-tert-butyl-3-(3,4-dimethylphenyl)3H-benzofuran-2-one and 10% of 5,7-di-tert-butyl-3-(2,3-dimethylphenyl)3H-benzofuran-2-one, and/or polymeric lactones as reported by Xia.

Component C—Phenolics

It is preferred that the phenolic be a liquid or that where there is a mixture of phenolics used the mixture itself is a liquid (thus a combination of solid and liquid phenolics resulting in a liquid mixture is desirable). Examples of component (C) includes the following:

Alkylated monophenols, for example 2,6-di-tert-butyl-4-methylphenol, 2-tert-butyl-4,6-dimethylphenol, 2,6di-tert-butyl-4-ethylphenol, 2,6-di-tert-butyl-4-n-butylphenol,2,6-di-tert-butyl-4-isobutylphenol, 2,6-dicyclopentyl-4-methylphenol, 2-(α-methylcyclohexyl)-4,6-dimethylphenol, 2,6-dioctadecyl4-methylphenol, 2,4,6-tricyclohexylphenol, 2,6-di-tert-butyl-4-methoxymethylphenol, 2,6-dinonyl-4-methylphenol, 2,4-dimethyl-6-(1-methylundec-1'-yl)phenol, 2,4-dimethyl-6-(1'-methylheptadec-1'-yl)phenol2,4-dimethyl-6-(1'-methyltridec-1'-yl) phenol and mixtures thereof.

Alkylthiomethilphenols, for example 2,4-dioctylthiomethyl-6-tert-butylphenol, 2,4-dioctylthiomethyl-6-methylphenol, 2,4-dioctylthiomethyl-6-ethylphenol, and 2,6-didodecylthiomethyl-4-nonylphenol.

Hydroxylated thiodiphenyl ethers, for example 2,2'-thiobis(6-tert-butyl-4-methylphenol), 2,2'-thiobis (4-octylphenol), 4,4'-thiobis (6-tert-butyl-3-methylphenol), 4,4'-thiobis (6-tert-butyl-2-methylphenol), 4,4'-thiobis-(3,6-di-sec-amylphenol), and 4,4'-bis-(2,6-dimethyl-4-hydroxyphenyl) disulfide.

Alkylidenebisphenols, for example 2,2'-methylenebis (6-tert-butyl-4-methylphenol), 2,2'-methylenebis(6-tert-butyl-4-ethylphenol), 2,2'-methylenebis [4-methyl-6-(α-methylcyclohexyl) phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis [6-(α, α-dimethylbenzyl)-4-nonylphenol], 4,4'-methylenebis(2,6-di-tert-butylphenol), 4,4'-methylenebis(6-tert-butyl-2-methylphenol), 1,1-bis (5-tert-butyl-4-hydroxy-2-methylphenyl)butane, 2,6-bis (3-tert-butyl-5-methyl-2-hydroxybenzyl)4-methylphenol, 1,1,3-tris(5-tert-butyl-4-hydroxy-2-me thylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis (3-tert-butyl-4-hydroxy-5-methyl-phenyl)dicyclopentadiene, bis[2-(3'-tert-butyl-2'-hydroxy-5'-methylbenzyl)-6-tert-butyl-4-methylphen yl] terephthalate, 1,1-bis-(3,5-dimethyl-2-hydroxphenyl) butane, 2,2-bis-( 3,5-di-tert-butyl-4-hydroxyphenyl) propane, 2,2-bis-(5-tert-butyl-4-hydroxy2-methylphenyl)-4-n-dodecylmercaptobutane, and 1,1,5,5-tetra-(5-tert-butyl-4-hydroxy2-methylphenyl) pentane.

O-, N- and S-benzyl compounds, for example 3,5,3',5'-tetra-tert-butyl-4,4'-dihydroxydibenzyl ether, octadecyl-4hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithio-terephthalate, bis(3,5-di-tert-butyl-4-hydroxybenzyl) sulfide, and isooctyl-3,5 di-tert-butyl-4-hydroxybenzylmercaptoacetate.

Aromatic hydroxybenzyl compounds, for example 1,3,5-tris-(3,5 -di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

Triazine Compounds, for example 2,4-bis(octylmercapto)-6-(3,5-di-tert-butyl-4-hydroxyanilino)-1,3,5-triazine, 2-octylmercapto-4,6-bis (3,5-di-tert-butyl-4'-hydroxyanilino)-1,3,5-triazine, 2-octylmercapto-4,6-bis (3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-trazine, 1,3,5-tris(3,5di-tert-butyl-4-hydroxyphenylpropionyl)-hexahydro-1,3, 5-triazine, and 1,3,5-tris(3,5-dicyclohexyl-4-hydroxybenzyl) isocyanurate.

Esters of β-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3 thiaundecanol, 3-thiapentadecano, trimethylhexanediol, trimethylolpropane, 4-hydroxymethyl-1-phospha-2,6,7-trioxabicyclo[2.2.2] octane.

In an embodiment of the present invention, component C is a 3-(3,5-bis(1,1-di-methjylethyl)4-hydroxy-phenyl) (C7-C9) alkyl (branched) propanoate (CAS: 125643-61-0) and/or benzenepropanoic acid, 3,5-bis(1,1-dimethylethyl)-4-hydroxy-, C13-15-branched and linear alkyl esters (CAS: 171090-93-0) and/or other phenolic blends such that a liquid form is made. Further specific examples of Component C include esters of β-(3,5-di-tert-butyl-4-hydroxylphenyl) propionic acid with mono- or polyhydric alcohols.

Component D—Tocopherols

In an embodiment of the present invention, component D is α-tocopherol, β-tocopherol, γ-tocopherol, δ-tocopherol or mixtures thereof (Vitamin E).

Component E—Phosphite Compounds

Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol. In an embodiment of the present invention, component E is triphenyl phosphite, a diphenyl alkyl phosphite, a phenyl dialkyl phosphite, or tris(nonylphenyl phosphite).

General and preferred ranges of components present in the inventive blend are as follows, given as weight percent of the additive:

TABLE A

| Components | General Range | Preferred Range 1 | Preferred Range 2 | Preferred Range 3 |
|---|---|---|---|---|
| A | 1-30 | 1-30 | 1-20 | 1-25 |
| B | 1-25 | 1-25 | 1-20 | 1-25 |
| C | 5-80 | 5-70 | 50-70 | 25-80 |
| D | 0-30 | 0-30 | 0-20 | 1-25 |
| E | 0-25 | 0-25 | 0-20 | 0-20 |

Finally, the combination of any embodiment or feature mentioned herein with one or more of any of the other separately mentioned embodiments or features is contemplated to be within the scope of the instant invention.

EXAMPLES

Example 1

Preparation of the Blend and Evaluation

Typically a blend of the aforementioned components is prepared by adding solid components to a heated blend (50-90° C.) of liquid components. The mixture is then charged into a polyether polyol (or polyester or blend). Commercially available polyether polyols have properties such that they are typically transparent, viscous liquids with a range of functionalities of about ~3, a hydroxyl number range of approximately 30-56, and glycine initiated with an ethylene oxide-propylene oxide (RD/PO) ratio of 10/90. The polyether polyol, antioxidant blend is considered a finished product to polyether polyol producers and can be used to prepare polyurethane foam products as described earlier. The finished product is preferably characterized by no or minimal discoloration caused by the antioxidant blend. The charge level of the inventive blend in the polyether polyol may vary from 0.05 to 2 pbw, or up to 4 pbw. A typical foam formula used for VDA-278 testing is low water (~3-4.5 pbw) and can conveniently be poured into a common cakebox as often done in the industry for testing.

TABLE 1

| Commercial example of Foam formula ingredient | Foam formula ingredient | pbw |
|---|---|---|
| VORANOL Triol Polyether Polyols | polyol | 100 |
| Water | Water | 4.3 |
| Niax Silicone L5770 | Silicone | 0.9 |
| Niax* Catalyst A-33 | Amine catalyst | 0.17 |
| Dabco ® T9 | Tin catalyst | 0.25 |
| Scorch inhibitor | Cited in text (preferred blends) | 0.05-4 |
| VORANATE ™ T-80 TDI | Toluene diisocyanate | 54.91 |

Foams prepared are sliced and swatches are conditioned for a seven day period of time prior following VDA-278 protocol.

Example 2

TABLE 2 below shows Brightmeter Color Readings (L, a, b) for SCORCH test of Blends #2, 3, 6 and 7, trialed against an incumbent scorch inhibitor formula (PUR 67). Here, "MA" and ResinD are forms of polymerized 1,2-dihydro-2,2,4-trimethylquinoline (component (A)). "1315" refers to Anox 1315 (component (C)). "1135" refers to Songox 1135 (component (C)). "VitaE" refers to vitamin E (component (D)). "AOX1" refers to Milliguard AOX1 (component (B)), a lactone based antioxidant made by the Milliken Co. (see, e.g., Xia).

Polyurethane foam formula used: Voranol 9137ca (Dow) 100 parts, Water 6 parts, Momentive L5570 Silicone 1.1 parts, Momentive A33 Amine 0.12 parts, Air Products T9 Tin Cat 0.2 parts, Voranate TDI (Dow) 78.0 parts.

TABLE 2

| | PUR 67 | Blend#2 10% MA (A) 30% 1315 (C) 50% VitaE (D) 10% AOX1(B) | Blend#3 10% ResinD (A) 40% 1315 (C) 40% VitaE (D) 10% AOX1(B) | Blend#6 10% ResinD (A) 40% 1315 (C) 20% 1135 (C) 20% VitaE (D) 10% AOX1 (B) | Blend#7 10% ResinD (A) 20% 1315 (C) 50% VitaE (D) 10% AOX1 (B) |
|---|---|---|---|---|---|
| 7:20@30% | | | | | |
| L | 82.71 | 81.88 | 81.15 | 81.91 | 83.03 |
| A | .21 | −.69 | −.54 | −.70 | −.73 |
| B | .00 | 3.95 | 3.84 | 4.1 | 3.99 |
| L | 66.37 | 76.62 | 81.78 | 68.47 | 65.06 |
| A | 7.95 | 0.81 | −2.57 | 6.41 | 9.01 |
| B | 33.24 | 23.96 | 15.85 | 31.52 | 34.23 |
| ΔE | 38.22 | 25.04 | 16.35 | 35.50 | 39.89 |
| Cream/Rise/Temp | 24/81/416 | 23/80/395 | 24/81/388 | 22/82/418 | 22/78/429 |

Example 3

Light Fade Study

TABLE 3 below shows Brightmeter Color Readings (L, a, b) for LIGHT EXPOSURE test of Blends #10-14, trialed against PUR 67.

TABLE 3

| | PUR 67 | Blend#10<br>15% ResinD (A)<br>40% 1315 (C)<br>35% VitaE (D)<br>10% AOX1 (B) | Blend#11<br>15% ResinD (A)<br>40% 1315 (C)<br>40% VitaE (D)<br>5% AOX1 (B) | Blend#12<br>19% ResinD (A)<br>40% 1315 (C)<br>40% VitaE (D)<br>1% AOX1 (B) | Blend#13<br>20% ResinD (A)<br>40% 1315 (C)<br>40% VitaE (D) | Blend#14<br>10% ResinD (A)<br>40% 1315(C)<br>40% VitaE (D)<br>10% AOX1(B) |
|---|---|---|---|---|---|---|
| 7:20 @30% | | | | | | |
| L | 81.49 | 80.32 | 78.83 | 79.85 | 80.85 | 81.09 |
| A | .48 | .69 | .70 | .63 | .63 | .58 |
| B | −.26 | −.48 | −.40 | −.29 | −.08 | 0.16 |
| 5 Days | | | | | | |
| L | 79.45 | 78.22 | 77.31 | 78.61 | 78.22 | 78.81 |
| A | .15 | .12 | .15 | .17 | .21 | .16 |
| B | 9.31 | 9.11 | 8.86 | 9.74 | 9.56 | 9.08 |
| ΔE | 9.79 | 9.83 | 9.40 | 10.12 | 9.85 | 9.22 |
| 7 Days | | | | | | |
| L | 78.48 | 77.77 | 76.70 | 77.65 | 77.30 | 78.07 |
| A | .43 | .45 | .47 | .53 | .51 | .31 |
| B | 11.15 | 11.67 | 11.35 | 12.09 | 11.85 | 11.04 |
| ΔE | 11.80 | 12.42 | 11.94 | 12.57 | 12.29 | 11.29 |

Example 4

Scorch Test with vitamin E removed

TABLE 4 below shows Brightmeter Color Readings (L, a, b) for SCORCH test of Blends #18, 19 and 20, trialed against PUR 67.

TABLE 4

| | PUR 67 | Blend#18<br>20% ResinD (A)<br>75% 1315 (C)<br>5% AOX1 (B) | Blend#119<br>20% ResinD (A)<br>80% 1315 (C) | Blend#20<br>20% ResinD (A)<br>75% 1315 (C)<br>5% VitaE (Cargill<br>Tocopherols) (D) | PUR 67 Repeat |
|---|---|---|---|---|---|
| Apr. 25, 2016<br>7:20@30% | | | | | |
| L | 82.59 | 84.08 | 84.16 | 83.25 | |
| A | .21 | .07 | .01 | .02 | |
| B | .95 | .85 | .66 | 1.16 | |
| L | 65.51 | 62.80 | 65.74 | 68.38 | |
| A | 8.36 | 10.17 | 8.65 | 6.86 | |
| B | 34.13 | 34.95 | 34.79 | 32.72 | |
| ΔE | 39.45 | 41.82 | 39.99 | 36.69 | |
| Cream/Rise/Temp | 21/79/437 | 21/78/429 | 20/73/423 | 20/72/423 | |
| Apr. 26, 2016<br>6:30@30% | | | | | |
| L | 83.18 | 83.16 | 83.12 | 83.68 | |
| A | .14 | .35 | .16 | .19 | |
| B | −.24 | −.68 | −.69 | −.34 | |
| L | 66.34 | 68.18 | 76.16 | 66.72 | |
| A | 7.72 | 6.88 | −.00 | 7.31 | |
| B | 32.95 | 32.76 | 22.08 | 32.43 | |
| ΔE | 37.93 | 36.82 | 23.36 | 37.22 | |
| Cream/Rise/Temp | 19/85/420 | 23/88/421 | 23/88/404 | 22/85/434 | |
| Jun. 9, 2016<br>7:30@30% | | | | | |
| L | 82.58 | 82.91 | 82.45 | 82.06 | 82.66 |
| A | −.05 | −.13 | −.11 | −.28 | −.06 |
| B | −.12 | .85 | .49 | 1.45 | .32 |
| L | 81.72 | 67.89 | 57.54 | 67.63 | 83.00 |
| A | −.54 | 5.91 | 11.39 | 5.66 | −.97 |
| B | .99 | 30.84 | 34.59 | 30.14 | 2.71 |
| ΔE | 2.01 | 35.06 | 44.62 | 34.52 | 3.15 |
| Cream/Rise/Temp | 23/103/396 | 20/93/412 | 21/88/433 | 17/82/410 | 1886/388 |

Example 5

Scorch Test Comparing Prior Art and Individual Components with Inventive Blend Table 5 below shows Brightmeter Color Readings (L, a, b) for SCORCH test for additional blends, including inventive Blend "B" (Blend#26) and Blend "C" (Blend#25).

| Blend "B" (Blend#26) | Blend "C" (Blend#25) |
|---|---|
| (A)-20% polymerized 1,2-dihydro-2,2,4-trimethylquinoline | (A) 20% polymerized 1,2-dihydro-2,2,4-trimethylquinoline |
| (C) 50% Anox 1315 | (C) 35% Anox 1315 |
| (C) 20% Songox 1135 | (C) 35% Songox 1135 |
| (B) 10% AOX1 | (B) 10% AOX1 |

TABLE 5

|  | PUR 67 (0.25) | AOX1 (0.25) | Blend "B" (0.25) 20% ResinD 50% 1315 20% 1135 10% AOX1 | Blend "C" (0.25) 20% ResinD 35% 1315 35% 1135 10% AOX1 | Resin D (A) (0.25) Polymerized 1,2-dihydro-2,2,4-trimethylquinoline | Anox 1315 (C) (0.25) 3,5-bis(1,1-dimethylethyl)-4-hydroxy-benzenepropanoic acid | Songnox 1135 (C) (0.25) (3,5-bis(1,1-dimethyl)4-hydroxyphenyl) (C7-C9) alkyl(branched) propionate |
|---|---|---|---|---|---|---|---|
| 7:50@30% |  |  |  |  |  |  |  |
| L | 81.41 | 81.87 | 82.88 | 80.62 | 83.88 | 81.20 | 81.84 |
| A | −.20 | −.83 | −.26 | −.33 | .14 | −.66 | −.26 |
| B | 1.09 | 3.91 | 2.03 | 2.21 | 2.18 | 2.15 | .92 |
| L | 82.13 | 82.20 | 81.81 | 82.22 | 60.23 | 72.07 | 77.90 |
| A | −.84 | −1.11 | −1.33 | −1.18 | 9.95 | 3.00 | −.38 |
| B | 3.01 | 4.41 | 4.95 | 3.28 | 35.01 | 23.87 | 12.90 |
| ΔE | 3.53 | 4.89 | 5.54 | 3.86 | 43.13 | 26.65 | 14.13 |
| Cream/Rise/Temp | 16/79/400 | 18/85/406 | 17/83/393 | 18/87/404 | 17/90/416 | 17/85/395 | 17/95/398 |
| $^8/_{12}$ | 3.53 | 4.89 | 5.54 | 3.86 | 43.13 | 26.65 | 14.13 |
| $^8/_{11}$ | 1.68 | 2.67 | 4.72 | 10.23 | 14.59 | 5.53 | 5.16 |
| $^8/_{5}$ | 4.40 | 5.97 | 1.83 | 8.66 | 48.94 | 32.62 | 11.94 |
| AVERAGE (3xs) | 3.20 | 4.51 | 4.03 | 7.58 | 35.55 | 21.60 | 10.41 |

Foam: Voranol 9137ca (DOW) 100 parts, Water 6 parts, Momentive L5570 Silicone 1.1 parts, Momentive A33 Amine 0.12 parts, Air Products T9 Tin Cat 0.2 parts, Voranate TDI (Dow) 78.0 parts.

Example 6

Emissions Test

The inventive blends adequately protected against scorch development in polyurethan slabstock foam and give low VOC/fog emissions as detected in VDA-278 against incumbent product PUR 67. The test concerns two heat treatments of a swatch of foam followed by analysis. The first heat treatment (90° C. for 30 minutes) collects lower boiling components (VOC) and the second heat treatment (thermal desorption at 120° C. for 60 minutes) collects higher boiling components (FOG). The measurement of volatile compounds (VOC/FOG) is according to VDA 278 (Daimler Chrysler-PB VWL 709). An average is presented for ease of comparison representing two values from the "center" and edge of the foam block. The specimens (see Example 5) results present total "VOC", "Fog", and "Total AO" for three trial foams containing inventive blends and a control consisting of PUR 67. Total emissions are reduced for all three blends but as (3,5-bis(1,1-di-methylethyl)4-hydroxy-phenyl) (C7-C9) alkyl(Branched) propanoate is reduced in the scorch inhibitor blends the total emissions value drops (c. A<B<C) yet all blends showed less than half the total emissions of the Control blend (PUR 67). It is also observed that the other components while detected (or derivatives of them) were at low levels.

TABLE 6

| Average center and edge | Control Blend | Blend "A" 20% ResinD (A) 70% ANOX (C) 10% AOX1 (B) | Blend "B" 20% ResinD (A) 50% 1315 (C) 20% 1135 (C) 10% AOX1 (B) | Blend "C" ResinD (A) 35% 1315 (C) 35% 1135 (C) 10% AOX1 (B) |
|---|---|---|---|---|
| Total VOC | 0.8 | 5.1 | 5.6 | 4.9 |
| Total Fog | 164 | 44 | 59 | 83 |
| Total emissions | 165 | 49 | 65 | 88 |

Antioxidant levels detected VDA-278

Discussion

The present invention uses the lactone mentioned in Xia but improves upon scorch performance showing a synergistic effect, as seen by comparison of AOX1 versus "B". This (AOX1) demonstrates prior art concerning a low VOC scorch inhibitor.

As demonstrated in the Examples above, a fraction of the prior art material ($1/10^{th}$ of AOX1 polymeric lactone) is required in the present composition to achieve similar performance of prior art material. Blend "B" shows greater reduced scorch compared against prior art AOX1. The same blend outperforms all individual components.

Polymerized 1,2-dihydro-2,2,4-tirmethylquinoline is not a particularly useful antioxidant for scorch protection. Two problems were observed during development of the present inventive blends. Firstly it is a solid thereby needing to be dissolved for further use if it had any further use as a slab stock polyether polyol stabilizer. Secondly, polymerized 1,2-dihydro-2,2,4-tirmethylquinoline was found to be a poor scorch inhibitor in polyurethane foam. (Example 5). However, once dissolved in the inventive composition both problems were overcome.

Example 7

Additional Scorch Exposure Test

TABLE 7

|  | Vanox 945 | PUR 68 | PUR 68 Repeat | 20% MA (A) 33% 1315 (C) 37% VitaE (D) 10% AOX1 (B) | 20% MA (A) 33% 2920* 37% VitaE (D) 10% AOX1 (B) | 20% MA(A) 33% 1520** 37% VitaE (D) 10% AOX1 (B) |
|---|---|---|---|---|---|---|
| 7:50@30% |  |  |  |  |  |  |
| L | 81.95 | 81.77 | 81.97 | 81.64 | 82.65 | 81.75 |
| A | -.00 | -.11 | -.02 | -.05 | -.03 | -.12 |
| B | .64 | .89 | .63 | .59 | .76 | 1.33 |
| L | 76.21 | 82.05 | 82.49 | 82.44 | 82.92 | 82.37 |
| A | .06 | -2.27 | -1.48 | -3.51 | -3.29 | -3.01 |
| B | 20.85 | 8.90 | 4.80 | 9.73 | 7.77 | 8.54 |
| ΔE | 27.93 | 9.50 | 5.32 | 10.63 | 8.71 | 9.31 |
| Cream/Rise/Temp | 25/85/384 | 25/86/372 | 22/87/382 | 21/85/381 | 23/87/375 | 22/82/380 |

*IRGANOX 1520 (2-Methyl-4,6-bis(octylsulfanylmethyl)phenol)

What is claimed is:

1. A foam composition formed from 0.05 to 4 pbw of a scorch inhibitor composition in combination with a polyether polyol or a polyester or blend thereof at 100 pbw, wherein the scorch inhibitor composition is a liquid and comprises:

(A) a 2,2,4-trimethyl-1,2-dihydroquinoline compound, present at 1-30 weight % of the scorch inhibitor composition, (B) a liquid polymeric lactone composition consisting of liquid lactones and/or lactone derivatives compounded to form a liquid, present at 1-25 weight % of the scorch inhibitor composition, (C) a phenolic component in liquid form present at 5-80% of the scorch inhibitor composition, being a compound or blend of compounds chosen from the group consisting of (i) (3,5-bis(1,1-di-methylethyl)4-hydroxyphenyl) (C7-C9) alkyl (branched) propanoate;

(ii) 3,5-bis(1,1-dimethylethyl)-4-hydroxy-benzenepropanoic acid, C13-15-branched and linear alkyl esters;

(iii) esters of β-(3,5-di-tert-butyl-4-hydroxylphenyl) propionic acid with mono- or polyhydric alcohols; and (iv) octyl 3-(3,5-di-tert-butyl-4-hydroxyphenyl)propanoate, (D) optionally a tocopherol, and (E) optionally a phosphite compound.

2. The foam composition of claim 1, wherein component (A) of the scorch inhibitor composition is chosen from the group consisting of 1,2-dihydro-2,2,4-trimethylquinoline polymer having 2 to 6 monomer units, non-aromatized 1,2-dihydro-2,2,4-trimethylquinoline composed of dimer and trimer units, 6-dodecyl-2,2,4-2,2,4-trimethyl-1,2-dihydroquinoline, 6-lauryl-2,2,4-trimethyl-1H-quinoline, 6-ethoxy-2,2,4-trimethyl-1-2-dihydroquinoline, polymerized 1,2-dihydro-2,2,4-trimethylquinoline, and a mixture thereof.

3. The foam composition of claim 1, wherein one or both of component (D) and component (E) is present and,
  a. Component (D), when present, comprises the tocopherol chosen from the group consisting of α-tocopherol, β-tocopherol, γ-tocopherol, δ-tocopherol and mixtures thereof, at a 1-30 weight % of the scorch inhibitor composition; and
  b. component (E), when present, comprises the phosphite compound chosen from the group consisting of a triphenyl phosphite, a diphenyl alkyl phosphite, a phenyl dialkyl phosphite, a tris(nonylphenyl) phosphite, a trilauryl phosphite, a trioctadecyl phosphite, a distearyl pentaerythritol diphosphite, a tris(2,4-di-tert-butylphenyl) phosphite, a diisodecyl pentaerythritol diphosphite, a bis(2,4-di-tert-butylphenyl) pentaerythritol diphosphite, a bis(2,6-di-tert-butyl-4-methylphenyl)-pentaerythritol diphosphite, a diisodecyloxypentaerythritol diphosphite, a bis(2,4-di-tert-butyl-6-methylphenyl)pentaerythritol, and a mixture thereof, at 1-25 weight % of the scorch inhibitor composition.

4. The foam composition of claim 1, wherein the scorch inhibitor composition consists essentially of a blend of components (A)-(E) or consists of a blend of components (A)-(E).

5. The foam composition of claim 1, which consists essentially of the scorch inhibitor composition and polyether polyol or a polyester or blend thereof, or which consists of the scorch inhibitor composition and polyether polyol or a polyester or blend thereof.

6. The foam composition of claim 1, wherein component (A) present at 1-25 weight % of the scorch inhibitor composition.

7. The foam composition of claim 1, wherein component (A) present at 1-20 weight % of the scorch inhibitor composition.

8. The foam composition of claim 1, wherein component (B) present at 1-20 weight % of the scorch inhibitor composition.

9. The foam composition of claim 1, wherein component (C) present at 5-70 weight % of the scorch inhibitor composition.

10. The foam composition of claim 1, wherein component (C) present at 25-80 weight % of the scorch inhibitor composition.

11. The foam composition of claim 1, wherein component (D) is present at 0-20 weight % of the scorch inhibitor composition.

12. The foam composition of claim 1, wherein component (D) is present at 0-25 weight % of the scorch inhibitor composition.

13. The foam composition of claim 1, wherein component (E) is present at 0-20 weight % of the scorch inhibitor composition.

14. The foam composition of claim 1, wherein
component (A) is present at 10-20 weight % of the scorch inhibitor composition,
component (B) is present at 1-10 weight % of the scorch inhibitor composition, and
component (C) is present at 20-50 weight % of the scorch inhibitor composition.

15. The foam composition of claim 1, wherein the scorch inhibitor composition comprises:
  (A) a polymerized 2,2,4-trimethyl-1,2-dihydroquinoline compound,
  (B) a liquid polymeric lactone composition consisting of liquid lactones and/or lactone derivatives compounded to form a liquid,
  (C) a phenolic component in liquid form, being a compound or blend of compounds chosen from the group consisting of
    (3,5-bis(1,1-di-methylethyl)4-hydroxyphenyl) (C7-C9) alkyl (branched) propanoate; and
    3,5-bis(1,1-dimethylethyl)-4-hydroxy-benzenepropanoic acid, C13-15-branched and linear alkyl esters.

16. A method for reducing scorch or for lowering emission profile during polyurethane foam production, comprising a step of adding 0.05 to 4 pbw of a scorch inhibitor composition, to polyether polyol or a polyester or blend thereof at 100 pbw
wherein the scorch inhibitor composition is a liquid and comprises:
  (A) a 2,2,4-trimethyl-1,2-dihydroquinoline compound, present at 1-30 weight % of the scorch inhibitor composition,
  (B) a liquid polymeric lactone composition consisting of liquid lactones and/or lactone derivatives compounded to form a liquid, present at 1-25 weight % of the scorch inhibitor composition,
  (C) a phenolic component in liquid form present at 5-80% of the scorch inhibitor composition, being a compound or blend of compounds chosen from the group consisting of
    (i) 3,5-bis(1,1-di-methylethyl)4-hydroxyphenyl) (C7-C9) alkyl (branched) propanoate;
    (ii) 3,5-bis(1,1-dimethylethyl)-4-hydroxy-benzenepropanoic acid, C13-15-branched and linear alkyl esters
    (iii) esters of β-(3,5-di-tert-butyl-4-hydroxylphenyl) propionic acid with mono- or polyhydric alcohols;
    (iv) octyl 3-(3,5-di-tert-butyl-4-hydroxyphenyl)propanoate,
  (D) optionally a tocopherol, and
  (E) optionally a phosphite compound.

* * * * *